(12) United States Patent
Werner et al.

(10) Patent No.: US 7,205,414 B2
(45) Date of Patent: Apr. 17, 2007

(54) PROCESS FOR THE KUMADA COUPLING REACTION

(75) Inventors: Christian Werner, Hannover (DE); Frauke Platz, Wölpinghausen (DE); Andreas Kanschik-Conradsen, Garbsen (DE)

(73) Assignee: Honeywell International Inc., Morristown, NJ (US)

( * ) Notice: Subject to any disclaimer, the term of this patent is extended or adjusted under 35 U.S.C. 154(b) by 278 days.

(21) Appl. No.: 11/033,573

(22) Filed: Jan. 12, 2005

(65) Prior Publication Data

US 2006/0155134 A1    Jul. 13, 2006

(51) Int. Cl.
*C07D 333/08* (2006.01)
*C07D 333/28* (2006.01)

(52) U.S. Cl. .............................. 549/80; 549/81; 549/83

(58) Field of Classification Search .................. 549/80, 549/81, 83
See application file for complete search history.

(56) References Cited

U.S. PATENT DOCUMENTS

| | | | | |
|---|---|---|---|---|
| 4,169,839 A | * | 10/1979 | Houbiers et al. | 549/81 |
| 4,889,940 A | * | 12/1989 | Grosvenor et al. | 549/81 |
| 5,371,240 A | * | 12/1994 | Slemon | 549/73 |
| 5,512,685 A | * | 4/1996 | Jarvinen et al. | 549/86 |
| 6,639,083 B1 | * | 10/2003 | Biard et al. | 549/83 |
| 6,676,857 B2 | * | 1/2004 | Heeney et al. | 252/500 |

FOREIGN PATENT DOCUMENTS

WO    WO 99/43684    9/1999

OTHER PUBLICATIONS

Tamao, K., et al. "Nickel-Phosphine Complex-Catalyzed Grignard Coupling-II." Tetrahedron Vo. 38, No. 22, pp. 3347-3354. Feb. 9, 1982.

* cited by examiner

*Primary Examiner*—Deborah C. Lambkin
(74) *Attorney, Agent, or Firm*—Roberts & Roberts, L.L.P.

(57) ABSTRACT

A method for the formation of 3-alkylthiophenes or 3-arylthiophenes from 3-halothiophenes. More particularly, improvements on the Kumada coupling reaction for the production of 3-alkylthiophenes or 3-arylthiophenes by reacting a 3-halothiophene with an alkylmagnesiumhalide or arylmagnesiumhalide Grignard reagent in the presence of a catalyst and a 2-methyl tetrahydrofuran solvent. The 2-methyl tetrahydrofuran solvent allows for higher concentrations of the Grignard reagent with minimal or no dithienyl side product generation, achieving higher product yields and at a lower cost than other known methods.

23 Claims, No Drawings

PROCESS FOR THE KUMADA COUPLING REACTION

BACKGROUND OF THE INVENTION

1. Field of the Invention

The invention relates to a method for the formation of 3-alkylthiophenes or 3-arylthiophenes from 3-halothiophenes. More particularly, the invention pertains to improvements on the Kumada coupling reaction for the production of 3-alkylthiophenes or 3-arylthiophenes.

2. Description of the Related Art

Alkyl and aryl substituted thiophenes are important intermediates for conductive polymers. Conducting polymers are materials that possess the electrical properties of metals yet retain the mechanical properties of polymers. Such conductive polymers are materials that are made conductive when combined with a doping material that facilitates polymer conductivity. This is commonly referred to in the art as "doping the polymer" and provides a lower energy threshold for conductivity. Doping materials suitable for doping of some conductive polymers include halogens such as iodine, bromine and chlorine. Recent years have lead to the development of conductive polymers that are even able to approach the conductivity of naturally conductive metals. Today, conductive polymers are particularly desirable materials for the fabrication of devices such as optical and electronic devices, electroluminescent devices, sensors and shielding materials.

The degree of conductivity exhibited by conductive polymers depends on the degree of order on a molecular level. This is due in part to the crystal lattice that allows an overlapping pathway for electrons. Included among polymers that have shown conductive properties when combined with appropriate doping materials are polythiophenes. Polythiophenes are particularly desirable because they effectively self-assemble into well-ordered, highly conducting nanoscale layers and have versatile properties that renders them useful for a wide range of commercial applications. However, one disadvantage of poly(thiophenes) is that they are not soluble, making them difficult to process. In order to increase the solubility and processability it is known to add alkyl chains in the 3-position, thereby obtaining a poly(3-alkylthiophene).

For example, in the article "Nickel-Phosphine Complex-Catalyzed Grignard Coupling II. Grignard Coupling of Heterocyclic Compounds" by Tamao, K.; Kodama, S.; Nakajima, I.; Kumada, M.; Minato, A.; and Suzuki, K (*Tetrahedron* 1982, 38, 3347–3354) (herein after "Kumada, et al."), cross-coupling reactions of heterocyclic halides with various Grignard reagents in the presence of nickel-phosphine complexes as catalysts are discussed. Particularly, the article discusses methods for introducing organic groups, e.g. alkyl groups, into halogenated heterocycles, such as five- and six-membered nitrogen or sulfur-containing heterocyclic compounds, using a nickel-phosphine catalyst complexes, such as [1,3-bis(diphenylphosphonyl)propane nickel(II) chloride] ($NiCl_2dppp$). According to Kumada, et al., reaction procedures are described teaching the introduction of an organic group onto the carbon atom of the heterocycle to which the halogen has been attached, giving an isomerically pure coupling product. The procedures described by Kumada, et al., however, have been found to generate an undesirable dithienyl byproduct that precipitates from reaction mixtures, thus limiting the desired product yield.

The present invention is an improved process for the coupling reactions described by Kumada, et al. The present invention provides a process for the preparation of 3-alkylthiophenes and 3-arylthiophenes at an exceptionally high yield.

Specifically, the invention describes a method for forming a 3-alkylthiophene or 3-arylthiophene which comprises reacting a 3-halothiophene with an alkylmagnesiumhalide Grignard reagent in the presence of a catalyst and a 2-methyl tetrahydrofuran solvent having a reagent concentration of at least about 0.5 mol/L in said solvent. It has unexpectedly been found that the use of a 2-methyl tetrahydrofuran solvent allows for higher concentrations of the Grignard reagent with minimal or no dithienyl side product generation. The resulting high yields (space yield, kg/l) of the desired 3-alkylthiophene reaction product are about five times the yield compared to the well known process described by Kumada, et al. The crude yield determined by gas chromatography of the reaction mixture or selectivity could be increased from about 70–80% up to about 97–99%.

SUMMARY OF THE INVENTION

The invention provides a method for forming a 3-alkylthiophene or 3-arylthiophene which comprises reacting a 3-halothiophene with either an alkylmagnesiumhalide or arylmagnesiumhalide Grignard reagent in the presence of a catalyst and a methyl-tetrahydrofuran solvent, wherein the Grignard reagent is present in an amount of at least about 0.5 mol/L relative to said solvent.

The invention also provides a method for forming a 3-alkylthiophene or 3-arylthiophene comprising:

a) forming either an alkylmagnesiumhalide or arylmagnesiumhalide Grignard reagent in a methyl-tetrahydrofuran solvent, the Grignard reagent being present in an amount of at least about 0.5 mol/L relative to said solvent;

b) separately forming a catalyst composition comprising a combination of a catalyst and a methyl-tetrahydrofuran solvent;

c) combining the catalyst composition with the Grignard reagent and the methyl-tetrahydrofuran solvent to form a reaction mixture; and d) thereafter, reacting a 3-halothiophene with said reaction mixture under conditions sufficient to produce either a 3-alkylthiophene or 3-arylthiophene reaction product.

DETAILED DESCRIPTION OF THE INVENTION

The invention provides an improved process for forming 3-alkyl or 3-aryl-substituted thiophenes from 3-halogen-substituted thiophenes. A traditional method of conducting this reaction is described in the Kumada, et al. article referenced above. The Kumada method involves the reaction of a 3-halothiophene with a Grignard reagent and nickel catalyst with a tetrahydrofuran solvent. However, the yield achieved through the Kumada reaction processes, or processes using THF, diethylether or methyl tertiary-butyl ether (MTBE) solvents, is limited due to the generation of dithienyl side-products that interfere with the coupling reaction. It has been unexpectedly found that the use of a methyl-tetrahydrofuran (methyl-THF) solvent, particularly 2-methyl-tetrahydrofuran, substantially reduces or altogether eliminates the formation of interfering side-products, allowing for higher concentrations of both the Grignard reagent and the catalyst, and achieving a nearly quantitative yield of alkylthiophene or arylthiophene. Methyl-THF is also preferred because it is much safer than other solvents because of its low tendency to form peroxides.

The Grignard reagent is prepared using commonly known techniques. Grignard reagents are extremely reactive substances made up of an organic group, e.g., an alkyl or aryl group joined by a highly polar covalent bond to magnesium, while the magnesium is joined by an ionic bond to a halogen ion, e.g., bromide or chloride. Grignard reagents are sensitive materials and generally are prepared just before use by reacting an organic halide, e.g., methyl bromide or bromodecane, with magnesium metal in an essentially completely dry solvent. Further, air is typically excluded from the reaction vessel, e.g., by flushing it with nitrogen.

In the process of the invention, the Grignard reagent is prepared by combining magnesium metal in a container (e.g. a flask) with methyl-tetrahydrofuran. In the preferred embodiment of the invention, the methyl-tetrahydrofuran solvent comprises 2-methyl-tetrahydrofuran. Also useful is 3-methyl-tetrahydrofuran. In the preferred embodiment of the invention, the magnesium metal and m-THF are combined at a mole ratio of from about 1:3 to about 1:6. Next, an organic halide, i.e. 1-bromoalkane such as 1-bromohexane, 1-bromodecane or 1-bromododecane, is added to the flask and reacted with the magnesium metal to form a compound having the formula RMgX, whereby R is either a $C_1$ to $C_{20}$ alkyl group or a $C_6$ to $C_{20}$ aryl group, and X is a halogen. It is within the scope of the invention that the alkyl or aryl groups could have greater than $C_{20}$ but the best results are anticipated with a $C_1$ to $C_{20}$ alkyl group or a $C_6$ to $C_{20}$ aryl group. In the preferred embodiment of the invention, R preferably comprises an alkyl group having from about 4 to about 20 carbon atoms. More preferably, R comprises an alkyl group having from about 6 to about 12 carbon atoms. This alkyl or aryl group will ultimately be substituted for the halogen group of the 3-halothiophene reactant, thus forming the 3-alkylthiophene or 3-arylthiophene of the invention. Accordingly, the type of Grignard reagent determines which alkylthiophene or arylthiophene is produced. In the preferred embodiment of the invention, the Grignard reagent is preferably an alkylmagnesiumhalide comprising either a hexylmagnesiumhalide, decylmagnesiumhalide or a dodecylmagnesiumhalide. Therefore, the preferred 3-alkylthiophenes of the invention are 3-hexylthiophene, 3-decylthiophene and 3-dodecylthiophene. In the formula RMgX, X may comprise any halogen, but preferably comprises either bromine, chlorine or iodine. Accordingly, the Grignard reagent of the invention preferably comprises an alkylmagnesiumbromide, alkylmagnesiumchloride or alkylmagnesiumiodide, or an arylmagnesiumbromide, arylmagnesiumchloride or arylmagnesiumiodide. Grignard reagents and their formation are well known in the art. In the preferred embodiment of the invention, the resulting Grignard reagent has a concentration in m-THF of from about 0.5 mol/L to about 5.0 mol/L, more preferably from about 2.0 mol/L to about 4.0 mol/L and most preferably from about 3.0 mol/L to about 3.5 mol/L.

Useful catalyst compositions for the invention are also well known. Preferred catalysts include those described in the Kumada, et al. article, which is incorporated herein by reference. Suitable catalysts include typical nickel and palladium catalysts that are well known in the art, including Ni(II), Ni(0), Pd(II) and Pd(0) compounds. In the preferred embodiment of the invention, the catalyst may comprise [1,3-bis(diphenylphosphino)propane]dichloronickel(II), nickel(II) acetylacetonate, 1,2-bis(diphenylphosphino)ethane nickel(II) chloride, dichlorobis(triphenylphosphine) palladium(II). Also preferred complexes of nickel(II) acetylacetonate and tri-tert-butylphosphine, triadamantylphosphine, 1,3-bis(2,4,6-trimethylphenyl)imidazolium chloride, 1,3-bis(2,6-diisopropylphenyl), 1,3-bis(2,6-diisopropylphenyl)imidazolium chloride, 1,3,4-triphenyl-4,5-dihydro-1H-1,2,4-triazol-5-ylidene, 1,3-diadamantyl-imidazolium chloride, 1,3-bis(2,4,6-trimethylphenyl)-imidazolidinium chloride, 1,3-bis(2,6-diisopropylphenyl)-imidazolidinium chloride and suspensions and combinations thereof, as well as suspensions and combinations of any of the above. The most preferred catalyst is 1,3-diphenylphosphinopropanenickel dichloride (Ni(dppp)$Cl_2$).

The catalyst composition of the invention may be in the form of a suspension or a solution. The catalysts above generally consist as suspensions in methyl-tetrahydrofuran. However, a catalyst solution may be formed by adding a portion of the Grignard reagent to a catalyst-m-THF suspension. In the preferred embodiment, a catalyst solution is formed by adding from about 0.9 equivalents to about 3.0 equivalents of the Grignard reagent compared to the catalyst compound, more preferably from about 1.5 to about 2.5 equivalents of said Grignard reagent compared to the catalyst compound. Overall, the catalyst preferably comprises a catalyst compound concentration of from about 0.001 mol % to about 10 mol % in said solvent, more preferably from about 0.01 mol % to about 1.0 mol %, and most preferably from about 0.09 mol % to about 0.1 mol % in said solvent. Most preferably, the catalyst composition is a suspension of a catalyst compound in methyl-THF, which catalyst compound preferably comprises a concentration of from about 1% by weight to about 50% by weight of said solvent.

The 3-alkylthiophenes or 3-arylthiophenes of the invention are formed by reacting a 3-halothiophene reactant with the alkylmagnesiumhalide or arylmagnesiumhalide Grignard reagent described herein in the presence of the catalyst. This reaction is known as a metathesis reaction. The halothiophenes may comprise any 3-halogenated thiophene, but the halogen is typically bromine, chlorine or iodine. In the preferred embodiment of the invention, the 3-halothiophene comprises either 3-bromothiophene or 3-chlorothiophene.

The reaction processes of the invention may be conducted by first combining the catalyst composition and Grignard reagent, and then adding the 3-halothiophene.

Alternately, the 3-halothiophene may be combined with the Grignard reagent followed by addition of the catalyst composition, or first combined with the catalyst composition followed by addition of the Grignard reagent. These sequences of steps are intended as exemplary and are not intended to be limiting. Additional examples of reaction steps are described in the Examples below. For example, in Example 3, magnesium metal and 1-bromodecane are combined in a 100% 2-methyl-tetrahydrofuran solvent along with a Nickel(II) catalyst. Thereafter, 3-bromothiophene is added to the flask.

The 3-halothiophene may be added neat or with a solvent such as methyl-THF. Preferably, the 3-halothiophene is added at a halothiophene to Grignard reagent mol ratio of from about 0.7:1 equivalents to about 1.2:1 equivalents, more preferably from about 0.75:1 eq. to about 1:1 eq., and most preferably from about 0.8:1 eq. to about 0.85:1 eq. Each of the reactions discussed above, i.e. the formation of the Grignard reagent and the Grignard metathesis coupling reaction, are preferably conducted at reaction temperatures of from about −20° C. to about 100° C., with a more preferred reaction temperature range of about 0° C. to about 20° C., and a most preferred range of from about 15° C. to about 20° C. The process results in a nearly quantitative yield of 3-alkylthiophene or 3-arylthiophene, greater than that achieved in any prior art process.

The processes of the invention are described with more specificity in the following non-limiting Examples.

Reaction Scheme

A preferred reaction scheme for the process of the invention is as follows:

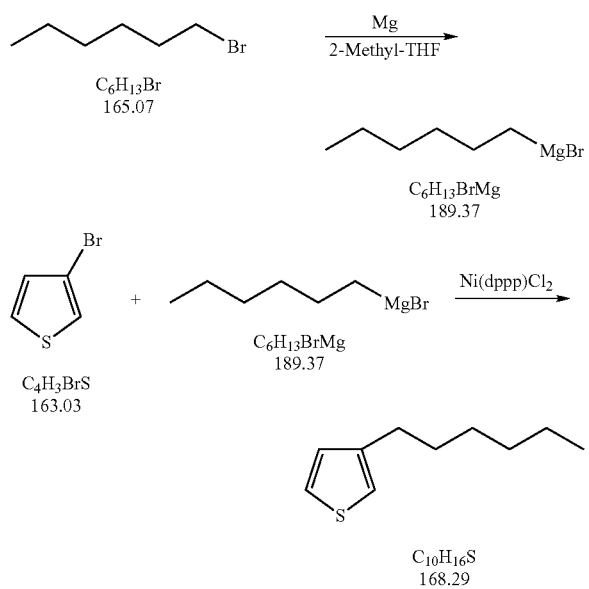

EXAMPLE 1

Added to a flask are 57.1 g (2.35 mol) of magnesium metal and 700 ml of 2-methyl-tetrahydrofuran. The flask contents are heated to 60–70° C. A reaction is initiated by adding 5 ml of hexylmagnesiumbromide (1 N) in 2-methyl-tetrahydrofuran to the flask. The Grignard reagent concentration in the solvent is 3.35 mol/L. The flask temperature is increased to 80–85° C. Next, 396 g of bromohexane (2.4 mol) is added to the flask over a period of 2.5 hours. The flask is then heated to reflux and stirred for an additional two hours. After two hours, the flask is cooled down to 15–20° C. Thereafter, add a suspension of 1.6 g of Ni(dppp)Cl$_2$ catalyst in 5 ml of 2-methyltetrahydrofuran. Next, over a period of four hours, add 326.1 g (2 mol) of 3-bromothiophene. Let this stir for an additional 16 hours. The reaction mixture is then hydrolyzed on 1000 ml HCl (10% w/w). A 100% conversion is achieved with essentially no bis-thienyl side-product, and a crude assay of 98.5%.

According to this procedure 5 runs were carried out.

| Run No. | Scale 3-Bromo-thiophene | 3-Bromo-thiophene | 3-Hexyl-thiophene | 3-(1-Methyl-pentyl)thiophene | Bis-thienyl |
|---|---|---|---|---|---|
| 1 | 4 | 0% | 98.3% | 0.45% | 0.42% |
| 2 | 4 | 0% | 98.88% | 0.38% | 0.15% |
| 3 | 4 | 0% | 98.49% | 0.39% | 0.49% |
| 4 | 4 | 0% | 96.76% | 0.39% | 0.44% |
| 5 | 116 | 0% | 97.6% | 0.37% | 0.16% |

EXAMPLE 2

Added to a flask are 58.3 g (2.4 mol) of magnesium metal and 500 ml of 2-methyl-tetrahydrofuran. The flask contents are heated to 60–70° C. A reaction is initiated by adding 5 ml of hexylmagnesiumbromide (1 N) in 2-methyl-tetrahydrofuran to the flask. The Grignard reagent concentration in the solvent is 4.8 mol/L. The flask temperature is increased to 80–85° C. Next, 396.2 g of bromohexane (2.4 mol) is added to the flask over a period of 2.5 hours. The flask is then heated to reflux and stirred for an additional two hours. After one hour, the flask is cooled down to 15–20° C. Thereafter, add a suspension of 1.6 g of Ni(dppp)Cl$_2$ catalyst in 5 ml of 2-methyltetrahydrofuran. Next, over a period of four hours, add 326.1 g (2 mol) of 3-bromothiophene. Let this stir for an additional 16 hours. The reaction mixture is then hydrolyzed on 1000 ml HCl (10% w/w). A 100% conversion is achieved with no bis-thienyl side-product, and a crude assay of 98.5%. Immediate gas chromatography of the reaction product showed 15.4% 3-bromothiophene, 81.1% 3-hexylthiophene and 0.0% bis-thienyl side-product. GC after one hour showed 8.7% 3-bromothiophene, 88.0% 3-hexylthiophene and 0.0% bis-thienyl side-product. GC after 15 hours showed 0.0% 3-bromothiophene, 97.5% 3-hexylthiophene, 0.0% bis-thienyl side-product and 0.41% 3-(1-methyl-pentyl)thiophene.

EXAMPLE 3

1.2 mol of magnesium metal and 1.2 mol of 1-bromodecane are combined in a 100% 2-methyl-tetrahydrofuran solvent, and with 300 mg of (1,3-bis (diphenylphosphino) propane)dichloro Nickel(II) catalyst. The Grignard reagent concentration in the solvent is 2.6 mol/L. Next, 3-bromothiophene (1 eq.) is added to the flask. The reactions were conducted at room temperature. Immediate gas chromatography of the reaction product showed 27.1% 3-bromothiophene, 30.0% 3-decylthiophene and 0.9% bis-thienyl side-product. GC after one hour showed 0.0% 3-bromothiophene, 92.6% 3-decylthiophene and 2.3% bis-thienyl side-product. GC after 2.5 hours showed 0.0% 3-bromothiophene, 94.6% 3-decylthiophene and 1.9% bis-thienyl side-product.

EXAMPLE 4 (COMPARATIVE)

A hexylmagnesiumbromide Grignard reagent (1 eq.) was added to mixture of a 50:50 tetrahydrofuran/toluene solvent, 3-bromothiophene (1 eq.) and 200 mg of a dichloro-bis (triphenylphosphine) palladium(II) catalyst. The Grignard reagent concentration in the solvent is 1 mol/L. The reaction was conducted at 80° C.

Immediate gas chromatography (GC) of the reaction product showed 15.2% 3-bromothiophene, 38.0% 3-hexylthiophene and 17.9% bis-thienyl side-product. GC after one hour showed 2.0% 3-bromothiophene, 40.7% 3-hexylthiophene and 23.9% bis-thienyl side-product. GC after 2.5 hours showed 1.3% 3-bromothiophene, 42.1% 3-hexylthiophene, 24.3% bis-thienyl side-product and 2.53% 3-(1-methylpentyl)thiophene. This results show a low selectivity using a dichloro-bis(triphenylphosphine) palladium(II) catalyst and 50:50 THF/toluene solvent. Also an undesirable amount of bis-thienyl and 3-(1-methylpentyl)thiophene side products.

EXAMPLE 5 (COMPARATIVE)

A hexylmagnesiumbromide Grignard reagent (1 eq.) was added to a mixture of a 50:50 THF/toluene solvent, 3-bromothiophene (1 eq.) and 200 mg of a dichloro-bis(triphenylphosphine) nickel(II) catalyst. The Grignard reagent concentration in the solvent is 1 mol/L. The reaction was conducted at room temperature. Immediate gas chromatography of the reaction product showed 7.1% 3-bromothiophene, 66.8% 3-hexylthiophene and 12.6% bis-thienyl side-product.

GC after one hour showed 2.2% 3-bromothiophene, 70.4% 3-hexylthiophene and 13.3% bis-thienyl side-product. GC after 2.5 hours showed 2.1% 3-bromothiophene, 68.8% 3-hexylthiophene, 14.0% bis-thienyl side-product and 0.23% 3-(1-methylpentyl)thiophene. The results show better selectivity using a dichloro-bis(triphenylphosphine) nickel(II) catalyst and 50:50 THF/toluene solvent than in Example 5, but incomplete conversion and an undesirable amount of bis-thienyl side product.

EXAMPLE 6 (COMPARATIVE)

A hexylmagnesiumbromide Grignard reagent (1 eq.) was added to a mixture of a 100% tetrahydrofuran solvent, 3-bromothiophene (1 eq.) and with 200 mg of a dichloro-bis(triphenylphosphine) nickel(II) catalyst. The Grignard reagent concentration in the solvent is 1 mol/L. The reaction was conducted at 60° C. Immediate gas chromatography of the reaction product showed 9.6% 3-bromothiophene, 36.2% 3-hexylthiophene and 25.7% bis-thienyl side-product. GC after one hour showed 6.6% 3-bromothiophene, 38.6% 3-hexylthiophene and 27.1% bis-thienyl side-product. GC after 2.5 hours showed 3.3% 3-bromothiophene, 37.7% 3-hexylthiophene and 20.3% bis-thienyl side-product. The high temperature (60° C.) and 100% tetrahydrofuran solvent gave low selectivity, incomplete conversion, and an undesirable amount of bis-thienyl side product.

EXAMPLE 7 (COMPARATIVE)

A hexylmagnesiumbromide Grignard reagent (1 eq.) was added to a mixture of a 100% tetrahydrofuran solvent, 3-bromothiophene (1 eq.) and with 200 mg of a dichloro-bis(triphenylphosphine) nickel(II) catalyst. The Grignard reagent concentration in the solvent is 1 mol/L. The reaction was conducted at 0° C. Immediate gas chromatography of the reaction product showed 0.09% 3-bromothiophene, 82.7% 3-hexylthiophene and 6.6% bis-thienyl side-product. GC after one hour showed 0.09% 3-bromothiophene, 82.3% 3-hexylthiophene and 6.7% bis-thienyl side-product. GC after 2.5 hours showed 0.5% 3-bromothiophene, 81.5% 3-hexylthiophene and 6.4% bis-thienyl side-product. The low temperature (0° C.) gave satisfactory selectivity but an undesirable amount of bis-thienyl side product.

EXAMPLE 8 (COMPARATIVE)

3-Bromothiophene (1 eq.) is reacted with a hexylmagnesiumbromide Grignard reagent (1.2 eq.) in a 100% diethyl-ether solvent and with 200 mg of a dichloro-bis(triphenylphosphine) nickel(II) catalyst. The Grignard reagent concentration in the solvent is 2 mol/L. The reaction was conducted at room temperature. Immediate gas chromatography of the reaction product showed 0.2% 3-bromothiophene, 74.3% 3-hexylthiophene and 10.5% bis-thienyl side-product. GC after one hour showed 0.1% 3-bromothiophene, 73.6% 3-hexylthiophene and 11.85% bis-thienyl side-product. GC after 2.5 hours showed 0.3% 3-bromothiophene, 73.3% 3-hexylthiophene, 10.7% bis-thienyl side-product and 0.09% 3-(1-methylpentyl) thiophene. The diethylether solvent gave complete conversion but selectivity was only ~70% and an undesirable amount of bis-thienyl side product was formed.

EXAMPLE 9 (COMPARATIVE)

3-Bromothiophene (1 eq.) is reacted with a hexylmagnesiumbromide Grignard reagent (1.2 eq.) in a 100% diethyl-ether solvent and with 200 mg of a (1,3-bis (diphenylphosphino)propane)dichloro Nickel(II) catalyst. The Grignard reagent concentration in the solvent is 2 mol/L. The reaction was conducted at room temperature. Immediate gas chromatography of the reaction product showed 0.1% 3-bromothiophene, 91.2% 3-hexylthiophene and 0.13% bis-thienyl side-product. GC after one hour showed 0.2% 3-bromothiophene, 90.0% 3-hexylthiophene and 0.2% bis-thienyl side-product. GC after 2.5 hours showed 0.16% 3-bromothiophene, 90.7% 3-hexylthiophene, 0.2% bis-thienyl side-product and 0.4% 3-(1-methylpentyl)thiophene. The diethylether solvent and (1,3-bis (diphenylphosphino) propane)dichloro Nickel(II) catalyst gave a selectivity of ~90%. This reaction mixture undesirably forms a solid at the 2 mol/L concentration and therefore cannot be worked up in a plant scale due to the inability of the solid to be purged on water, which then requires the addition of water to the reaction. This may lead to accumulation of water which can suddenly react, leading to uncontrolled development of heat, and presenting serious safety concerns.

EXAMPLE 10 (COMPARATIVE)

3-Bromothiophene (1 eq.) is reacted with a hexylmagnesiumbromide Grignard reagent (1.2 eq.) in a 100% diethyl-ether solvent and with 200 mg of a dichloro-bis(triphenylphosphine) palladium(II) catalyst. The Grignard reagent concentration in the solvent is 2 mol/L. The reaction was conducted at room temperature. Immediate gas chromatography of the reaction product showed 77.2% 3-bromothiophene, 4.2% 3-hexylthiophene and 0.5% bis-thienyl side-product.

GC after one hour showed 78.1% 3-bromothiophene, 4.0% 3-hexylthiophene and 0.2% bis-thienyl side-product. GC after 2.5 hours showed 76.8% 3-bromothiophene, 4.5% 3-hexylthiophene and 0.3% bis-thienyl side-product.

The diethylether solvent and dichloro-bis(triphenylphosphino) palladium(II) catalyst gave a bad conversion percentage.

EXAMPLE 11 (COMPARATIVE)

3-Bromothiophene (1 eq.) is reacted with a hexylmagnesiumbromide Grignard reagent (1.2 eq.) in a 100% diethyl-ether solvent and with 200 mg of a dichloro-bis(triphenylphosphine) palladium(II) catalyst. The Grignard reagent concentration in the solvent is 2 mol/L. The reaction was conducted at 0° C. Immediate gas chromatography of the reaction product showed 0.09% 3-bromothiophene, 81.5% 3-hexylthiophene and 5.3% bis-thienyl side-product. GC after one hour showed 0.09% 3-bromothiophene, 82.5% 3-hexylthiophene and 5.1% bis-thienyl side-product. GC after 2.5 hours showed 0.07% 3-bromothiophene, 82.9% 3-hexylthiophene, 5.2% bis-thienyl side-product and 0.09% 3-(1-methylpentyl)thiophene. The diethylether solvent, 0° C. reaction temperature and dichloro-bis(triphenylphosphine) palladium(II) catalyst gave complete conversion and good selectivity (~80%), but 5.2% bis-thienyl side-product.

EXAMPLE 12 (COMPARATIVE)

3-Bromothiophene (1 eq.) is reacted with a hexylmagnesiumbromide Grignard reagent (1.2 eq.) in a 100% diethylether solvent and with 200 mg of a Nickel(II) acetylacetonate catalyst. The Grignard reagent concentration in the solvent is 2 mol/L. The reaction was conducted at room temperature. Immediate gas chromatography of the reaction product showed 60.0% 3-bromothiophene, 5.7% 3-hexylthiophene and 5.9% bis-thienyl side-product. GC after one hour showed 40.1% 3-bromothiophene, 12.7% 3-hexylthiophene, 16.2% bis-thienyl side-product and 2.4% 3-(1-methylpentyl)thiophene. The nickel(II) acetylacetonate catalyst and diethylether solvent gave incomplete conversion.

EXAMPLE 13 (COMPARATIVE)

3-Bromothiophene (1 eq.) is reacted with a hexylmagnesiumbromide Grignard reagent (1.2 eq.) in a 100% diethylether solvent and with 12.6 mg of a (1,3-bis (diphenylphosphino)propane)dichloro Nickel(II) catalyst. The Grignard reagent concentration in the solvent is 2 mol/L. The reaction was conducted at room temperature. Immediate gas chromatography of the reaction product showed 60.9% 3-bromothiophene, 27.2% 3-hexylthiophene and 0.3% bis-thienyl side-product. GC after one hour showed 45.6% 3-bromothiophene, 42.9% 3-hexylthiophene and 0.3% bis-thienyl side-product. GC after 2.5 hours showed 35.6% 3-bromothiophene, 51.8% 3-hexylthiophene, 0.3% bis-thienyl side-product and 0.31% 3-(1-methylpentyl)thiophene. A reduced amount of (1,3-bis (diphenylphosphino)propane)dichloro Nickel(II) catalyst and diethylether solvent gave incomplete conversion.

EXAMPLE 14 (COMPARATIVE)

3-Bromothiophene (1 eq.) is reacted with a hexylmagnesiumbromide Grignard reagent (1.2 eq.) in a 100% diethylether solvent and with no catalyst. The Grignard reagent concentration in the solvent is 2 mol/L. The reaction was conducted at room temperature. Immediate gas chromatography of the reaction product showed 85.7% 3-bromothiophene, 0.5% 3-hexylthiophene and 0.4% bis-thienyl side-product. GC after one hour showed 85.7% 3-bromothiophene, 1.1% 3-hexylthiophene and 0.2% bis-thienyl side-product. This shows almost no conversion with no catalyst.

EXAMPLE 15 (COMPARATIVE)

3-Bromothiophene (1 eq.) is reacted with a hexylmagnesiumbromide Grignard reagent (1.2 eq.) in a 100% diethylether solvent and with 12.6 mg of a dichloro-bis(triphenylphosphine) nickel(II) catalyst. The Grignard reagent concentration in the solvent is 2 mol/L. The reaction was conducted at room temperature. Immediate gas chromatography of the reaction product showed 85.3% 3-bromothiophene, 1.7% 3-hexylthiophene and 0.5% bis-thienyl side-product. GC after one hour showed 68.0% 3-bromothiophene, 3.1% 3-hexylthiophene, 6.3% bis-thienyl side-product and 0.89%. This shows bad conversion with a diethylether solvent and a dichloro-bis(triphenylphosphine) nickel(II) catalyst.

EXAMPLE 16 (COMPARATIVE)

3-Bromothiophene (1 eq.) is combined in a flask with 1.1 mol of magnesium metal and 1.15 mol of 1-bromohexane in a 100% THF solvent, and with 815 mg of a (1,3-bis (diphenylphosphino)propane)dichloro Nickel(II) catalyst in suspension. The Grignard reagent concentration in the solvent is 2.2 mol/L. The reactions were conducted at room temperature. Immediate gas chromatography of the reaction product showed 85.3% 3-bromothiophene, 1.7% 3-hexylthiophene and 0.5% bis-thienyl side-product. GC after 48 hours showed 2.9% 3-bromothiophene, 64.5% 3-hexylthiophene, 9.8% bis-thienyl side-product and 3.34% 3-(1-methylpentyl)thiophene. This shows bad selectivity with a 100% THF solvent.

EXAMPLE 17 (COMPARATIVE)

3-Bromothiophene (1 eq.) is combined in a flask with 1.2 mol of magnesium metal and 1.2 mol of 1-bromohexane in a 50:50 THF/MTBE solvent, and with 600 mg of a (1,3-bis (diphenylphosphino)propane)dichloro Nickel(II) catalyst in suspension. The Grignard reagent concentration in the solvent is 1.3 mol/L. The reactions were conducted at room temperature. Gas chromatography of the reaction product after 15 hours showed 0.2% 3-bromothiophene, 86.7% 3-hexylthiophene, 5.6% bis-thienyl side-product and 1.59% 3-(1-methylpentyl)thiophene. This shows high bis-thienyl and 3-(1-methylpentyl)thiophene side-product formation with a 50:50 THF/MTBE solvent. Overall, the comparative examples show that the main input factor for the selectivity is the catalyst, secondly the temperature and solvent is responsible for the final completion of the selectivity. Expressed in numbers: 60%, 30%, 10% responsibility. In methyl-THF, a Grignard reagent concentration of up to 4 mol/L is possible.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:
1. A method for forming a 3-alkylthiophene or 3-arylthiophene which comprises reacting a 3-halothiophene with either an alkylmagnesiumhalide or arylmagnesiumhalide Grignard reagent in the presence of a catalyst and a methyltetrahydrofuran solvent, wherein the Grignard reagent is present in an amount of at least about 0.5 mol/L relative to said solvent.
2. The method of claim 1 which comprises forming a 3-($C_1$ to $C_{20}$) alkylthiophene.
3. The method of claim 1 which comprises forming a 3-($C_6$ to $C_{20}$) arylthiophene.
4. The method of claim 1 wherein said Grignard reagent is present in an amount of from about 2.0 mol/L to about 4.0 mol/L relative to said solvent.
5. The method of claim 1 wherein said Grignard reagent is present in an amount of from about 3.0 mol/L to about 3.5 mol/L relative to said solvent.

6. The method of claim 1 wherein said solvent comprises 2-methyl-tetrahydrofuran.

7. The method of claim 1 wherein the Grignard reagent comprises a $C_4$ to $C_{20}$ alkyl magnesiumhalide.

8. The method of claim 1 wherein the Grignard reagent comprises a hexylmagnesiumhalide, a decylmagnesiumhalide, or a dodecylmagnesiumhalide.

9. The method of claim 1 wherein said catalyst comprises a material selected from the group consisting of Ni(II), Ni(0), Pd(II) and Pd(0) compounds and combinations thereof.

10. The method of claim 1 wherein said catalyst is selected from the group consisting of [1,3-bis(diphenylphosphino)propane]dichloronickel(II), nickel(II) acetylacetonate, 1,2-bis(diphenylphosphino)ethane nickel(II) chloride, dichlorobis(triphenylphosphine) palladium(II); complexes of nickel(II) acetylacetonate and tri-tert-butylphosphine, triadamantylphosphine, 1,3-bis(2,4,6-trimethylphenyl)imidazolium chloride, 1,3-bis(2,6-diisopropylphenyl), 1,3-bis(2,6-diisopropylphenyl)imidazolium chloride, 1,3,4-triphenyl-4,5-dihydro-1H-1,2,4-triazol-5-ylidene, 1,3-diadamantyl-imidazolium chloride, 1,3-bis(2,4,6-trimethylphenyl)-imidazolidinium chloride, 1,3-bis(2,6-diisopropylphenyl)-imidazolidinium chloride and combinations thereof.

11. The method of claim 1 wherein said reacting is conducted at a temperature of from about 15° C. to about 20° C.

12. A method for forming a 3-alkylthiophene or 3-arylthiophene comprising:
 a) forming either an alkylmagnesiumhalide or arylmagnesiumhalide Grignard reagent in a methyl-tetrahydrofuran solvent, the Grignard reagent being present in an amount of at least about 0.5 mol/L relative to said solvent;
 b) separately forming a catalyst composition comprising a combination of a catalyst and a methyl-tetrahydrofuran solvent;
 c) combining the catalyst composition with the Grignard reagent and the methyl-tetrahydrofuran solvent to form a reaction mixture; and
 d) thereafter, reacting a 3-halothiophene with said reaction mixture under conditions sufficient to produce either a 3-alkylthiophene or 3-arylthiophene reaction product.

13. The method of claim 12 which comprises forming a 3-($C_1$ to $C_{20}$) alkylthiophene.

14. The method of claim 12 which comprises forming a 3-($C_6$ to $C_{20}$) arylthiophene.

15. The method of claim 12 wherein said Grignard reagent is present in an amount of from about 2.0 mol/L to about 4.0 mol/L relative to said solvent.

16. The method of claim 12 wherein said Grignard reagent is present in an amount of from about 3.0 mol/L to about 3.5 mol/L relative to said solvent.

17. The method of claim 12 wherein said solvent comprises 2-methyl-tetrahydrofuran.

18. The method of claim 12 wherein said catalyst is present in an amount of from about 0.001 mol % to about 10 mol % relative to said solvent.

19. The method of claim 12 wherein the Grignard reagent comprises a $C_4$ to $C_{20}$ alkyl magnesiumhalide.

20. The method of claim 12 wherein said catalyst comprises a material selected from the group consisting of Ni(II), Ni(0), Pd(II) and Pd(0) compounds and combinations thereof.

21. The method of claim 12 wherein said polymerization catalyst is selected from the group consisting of [1,3-bis(diphenylphosphino)propane]dichloronickel(II), nickel(II) acetylacetonate, 1,2-bis(diphenylphosphino)ethane nickel(II) chloride, dichlorobis(triphenylphosphine) palladium(II); complexes of nickel(II) acetylacetonate and tri-tert-butylphosphine, triadamantylphosphine, 1,3-bis(2,4,6-trimethylphenyl)imidazolium chloride, 1,3-bis(2,6-diisopropylphenyl), 1,3-bis(2,6-diisopropylphenyl)imidazolium chloride, 1,3,4-triphenyl-4,5-dihydro-1H-1,2,4-triazol-5-ylidene, 1,3-diadamantyl-imidazolium chloride, 1,3-bis(2,4,6-trimethylphenyl)-imidazolidinium chloride, 1,3-bis(2,6-diisopropylphenyl)-imidazolidinium chloride and combinations thereof.

22. The method of claim 12 further comprising recovering 3-alkylthiophene or 3-arylthiophene from said reaction product.

23. The method of claim 12 wherein said reacting is conducted at a temperature of from about 15° C. to about 20° C.

* * * * *